United States Patent [19] [11] Patent Number: 5,095,025
Tanaka et al. [45] Date of Patent: Mar. 10, 1992

[54] BENZOTHIAZOLE DERIVATIVE

[75] Inventors: Ken-ichi Tanaka, Kita; Hiroshi Kawada, Kitasouma; Shinji Nishimura, Inashiki; Mitsumasa Yamazaki, Hasuda, all of Japan

[73] Assignee: Hodogaya Chemical Co., Ltd., Tokyo, Japan

[21] Appl. No.: 582,195

[22] PCT Filed: Jan. 31, 1990

[86] PCT No.: PCT/JP90/00113

§ 371 Date: Sep. 26, 1990

§ 102(e) Date: Sep. 26, 1990

[87] PCT Pub. No.: WO90/08765

PCT Pub. Date: Aug. 9, 1990

[30] Foreign Application Priority Data

Feb. 1, 1989 [JP] Japan ................... 1-20753

[51] Int. Cl.$^5$ .............. C07D 277/82; A01N 47/18; A01N 47/36; A01N 43/78
[52] U.S. Cl. .......................... 514/367; 548/163
[58] Field of Search ................... 548/163; 514/367

[56] References Cited

U.S. PATENT DOCUMENTS

| 3,671,531 | 6/1972 | Dixon | 260/305 |
|---|---|---|---|
| 3,807,985 | 4/1974 | Dixon | 71/90 |
| 4,970,318 | 11/1990 | Schaus | 516/195 |

FOREIGN PATENT DOCUMENTS

| 0245991 | 11/1987 | European Pat. Off. |
| 52-148071 | 12/1977 | Japan . |
| 53-9767 | 1/1978 | Japan . |
| 53-44561 | 4/1978 | Japan . |
| 63-190880 | 8/1988 | Japan . |
| 63-203672 | 8/1988 | Japan . |
| 1-93579 | 4/1989 | Japan . |
| 1-311071 | 12/1989 | Japan . |
| 1531052 | 11/1978 | United Kingdom . |

OTHER PUBLICATIONS

Jazodzinski et al., Chem. Abstracts, vol. 110, p. 447 (1989) Abstract No. 23046y.
Harlmann et al., Chem. Abstracts, vol. 105, p. 744 (1986) Abstract No. 172414r.
Rashkeo et al., Chem. Abstracts, vol. 94, p. 479 (1981) Abstract No. 29663v.
Regitz et al., Chem. Abstracts, vol. 92, p. 633 (1980) Abstract No. 76004a.
Rozhkova et al., Chem. Abstracts, vol. 84, p. 531 (1976) Abstract No. 121704a.
Akiba et al., Chem. Abstracts, vol. 83, p. 454 (1975) Abstract No. 177580d.
Horgan et al., Chem. Abstracts, vol. 82, p. 13 (1975) Abstract No. 164697b.
Bartsch et al., Chem. Abstracts, vol. 78, p. 387 (1973) Abstract No. 16088f.
Van Allan et al., Chem. Abstracts, vol. 69, p. 7216 (1968) Abstract No. 77169u.
Quast et al., Chem. Abstracts, vol. 69, p. 1097 (1968) Abstract No. 11402h.
Hueng et al., Chem. Abstracts, vol. 69, p. 1097 (1968) Abstract No. 11401g.
Balli et al., Chem. Abstracts, vol. 66, p. 4488 (1967) Abstract No. 47281v.
Quast et al., Chem. Abstracts, vol. 65, p. 7165 (1966) Abstract No. 7165f.
Hunig et al., Chem. Abstracts, vol. 52, p. 7297 (1958) Abstract No. 7297e.
Kutschy et al., Chem. Abstracts, vol. 109, p. 641 (1988) Abstract No. 54311q.
Fanghaenel et al., Chem. Abstracts, vol. 92, p. 615 (1980) Abstract No. 7830d.
Krasovskii et al., Chem. Abstracts, vol. 89, p. 615 (1978) Abstract No. 43217f.
Akiba et al., Chem. Abstracts, vol. 82, p. 424–425 (1975) Abstract No. 43233p.
Tamaru et al., Chem. Abstracts, vol. 80, p. 403 (1974) Abstract No. 95833n.
Akiba et al., Chem. Abstracts, vol. 77, p. 442 (1972) Abstract No. 74539u.
Dyson et al., Chem. Abstracts, vol. 25, pp. 4880–4881, (1931) Abstract No. 4881e.
Morgan, J. Med. Chem. 18 315 (1975).

*Primary Examiner*—Robert Gerstl
*Attorney, Agent, or Firm*—Wenderoth, Lind & Ponack

[57] ABSTRACT

A benzothiazole derivative represented by the general formula:

$$\begin{array}{c} Y \\ | \\ N \\ Z \end{array} \diagdown = NCOX$$

wherein
X represents —NHR, —R or —OR group in which R is a lower alkyl, cycloalkyl, aryl or substituted aryl group;
Y represents a lower alkyl, alkenyl, alkyloxycarbonylalkyl, benzyl or substituted benzyl group; and
Z represents a lower alkoxy group or a hydrogen atom.

This compound is useful as an active ingredient of an agricultural and horticultural fungicide.

5 Claims, No Drawings

BENZOTHIAZOLE DERIVATIVE

TECHNICAL FIELD

The invention relates to a benzothiazole derivative which is useful as an agricultural and horticultural fungicide.

BACKGROUND ART

Thanks to fertilizers, pesticides and various agricultural materials, a high productivity has been achieved in recent agriculture. On the other hand, there are some serious problems in this field including the appearance of chemical-tolerant strains caused by repetitive application of pesticides and disease damage caused by continuous cropping (i.e. by continuous annual culture of a single crop). Under these circumstances, it has been urgently required to develop a highly safe chemical. Thus, the present invention provides a means for solving these problems.

DISCLOSURE OF THE INVENTION

The present invention provides a benzothiazole derivative represented by the following general formula, and furthermore provides an agricultural and horticultural fungicide containing the benzothiazole derivative as an active ingredient:

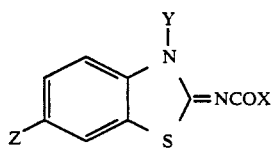

wherein X represents —NHR, —R or —OR group in which R is a lower alkyl, cycloalkyl, aryl or substituted aryl group;

Y represents a lower alkyl, alkenyl, alkyloxycarbonylalkyl, benzyl or substituted benzyl group; and Z represents a lower alkoxy group or a hydrogen atom.

The compound of the present invention may be synthesized in the following manner. First, a 2-aminobenzothiazole represented by the following general formula [I]:

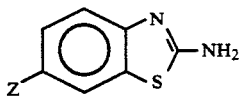

wherein Z is as defined above,
is reacted with the corresponding alkyl halide to thereby obtain a 3-substituted 2-iminobenzothiazole [II]:

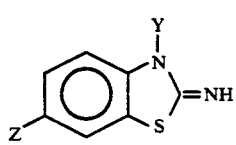

wherein Z and Y are each as defined above.

Next, the compound [II] is reacted with the corresponding isocyanate, acid halide or halogenoformate in an appropriate solvent.

BEST MODE FOR CARRYING OUT THE INVENTION

Examples of the organic solvent to be used in the reaction of the 3-substituted 2-iminobenzothiazole with the isocyanate include dioxane, tetrahydrofuran, acetone, methyl ethyl ketone, benzene, toluene, xylene, monochlorobenzene, dichlorobenzene, dimethylformamide, acetonitrile and the like. Furthermore, examples of a catalyst effective for this reaction include organometallic compounds such as dibutyltin dilaurate and tertiary amines such as triethylamine.

The solvent for the reaction between the 3-substituted 2-iminobenzothiazole and the acid halide or the halogenoformate may be selected from among those described above for the reaction of the 3-substituted 2-iminobenzothiazole with the isocyanate. Examples of a deacidifying agent effective for this reaction include tertiary amines such as triethylamine and alkali metal carbonates or alkaline earth metal carbonates such as sodium hydrogencarbonate, potassium carbonate and calcium carbonate.

The above-described reaction between the 3-substituted 2-iminobenzothiazole and the isocyanate, acid halide or halogenoformate may be preferably conducted at a temperature of from 0° to 100° C.

Now typical examples for the synthesis of the benzothiazole derivative of the present invention will be given. Table 1 summarizes the compounds thus synthesized.

SYNTHESIS EXAMPLE 1

Synthesis of 3-allyl-2-methoxycarbonyliminobenzothiazole (compound No. 4 in Table 1):

To a mixture comprising 3.8 g of 3-allyl-2-iminothiazole, 3.4 g of sodium hydrogencarbonate and 50 ml of tetrahydrofuran was added 1.9 g of methyl chloroformate dropwise at room temperature under stirring. After reacting for two hours, the reaction mixture was poured into approximately 200 ml of water. The crystals precipitated were collected by filtering to thereby obtain 4.5 g of the objective compound.

Yield: 91%.
m.p.: 121°–124° C.
IR (cm$^{-1}$): 1638.

SYNTHESIS EXAMPLE 2

Synthesis of 3-benzyl-2-[(N-cyclohexylcarbamoyl)-imino]benzothiazole (compound No. 13 in Table 1):

To a solution of 1.8 g of 3-benzyl-2-iminobenzothiazole and a catalytic amount of dibutyltin dilaurate in 30 ml of acetone was added 0.95 g of cyclohexyl isocyanate dropwise. After seven hours, the reaction mixture was poured into approximately 100 ml of water. The crystals precipitated were collected by filtering to thereby obtain 2.0 g of the objective compound.

Yield: 72%.
m.p.: 170.5°–173.5° C.
IR (cm$^{-1}$): 3425 and 1640.

SYNTHESIS EXAMPLE 3

Synthesis of 3-allyl-2-pivaloyliminobenzothiazole (compound No. 9 in Table 1):

To a solution of 2.0 g of 3-allyl-2-iminobenzothiazole and 1.5 g of triethylamine in 30 ml of tetrahydrofuran was added 1.3 g of pivaloyl chloride dropwise at room temperature under stirring. After reacting for five hours, the reaction mixture was poured into approximately 200 ml of water. The crystals precipitated were collected by filtering to thereby obtain 2.6 g of the objective compound.

m.p.: 60°–62° C.
IR (cm$^{-1}$): 1610.

TABLE 1

Compounds represented by general formula

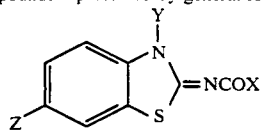

| Compound No. | X | Y | Z | m.p. (°C.) | IR spectrum (cm$^{-1}$) |
|---|---|---|---|---|---|
| 1 | —NHCH$_3$ | —CH$_3$ | H | 164~166 | 3370, 1610 |
| 2 | —NHCH$_3$ | —CH$_2$CH=CH$_2$ | H | 155~157 | 3350, 1613 |
| 3 | —NHCH$_3$ | —CH$_2$COOCH$_3$ | H | 202~203 | 3380, 1740, 1626 |
| 4 | —OCH$_3$ | —CH$_2$CH=CH$_2$ | H | 121~124 | 1638 |
| 5 | —NHCH$_2$CH$_3$ | —CH$_2$CH=CH$_2$ | H | 88~89 | 3290, 1620 |
| 6 | —NHCH$_2$CH$_2$CH$_3$ | —CH$_2$CH=CH$_2$ | H | oil | 3300, 1620 |
| 7 | —NHCH$_2$CH$_2$CH$_2$CH$_3$ | —CH$_2$CH=CH$_2$ | H | oil | 3300, 1620 |
| 8 | —C(CH$_3$)$_3$ | —CH$_3$ | H | 105~106 | 1604 |
| 9 | —C(CH$_3$)$_3$ | —CH$_2$CH=CH$_2$ | H | 60~62 | 1610 |
| 10 | —NHC(CH$_3$)$_3$ | —CH$_2$CH=CH$_2$ | H | 123.5~124.5 | 3405, 1636 |
| 11 | —NHCH(CH$_3$)$_2$ | —CH$_2$CH=CH$_2$ | H | oil | 3300~3400, 1630 |
| 12 | —NH—C$_6$H$_5$ | —CH$_2$COOCH$_3$ | H | 223~236 | 3420, 1730, 1645 |
| 13 | —NH—cyclohexyl | —CH$_2$—C$_6$H$_5$ | H | 168~170 | 3425, 1640 |
| 14 | —O—C$_6$H$_5$ | —CH$_2$CH=CH$_2$ | H | 144~146 | 1650 |
| 15 | —NH—cyclohexyl | —CH$_2$—C$_6$H$_4$—CH$_3$ | H | 131~133 | 3430, 1630 |
| 16 | —NH—cyclohexyl | —CH$_2$CH=CH$_2$ | H | 129~131 | 3340, 1630 |
| 17 | —NH—cyclohexyl | —CH$_2$—(2-CH$_3$-C$_6$H$_4$) | H | 211~214 | 3425, 1635 |

TABLE 1-continued

Compounds represented by general formula

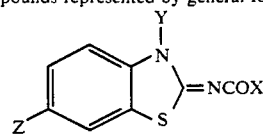

| Compound No. | X | Y | Z | m.p. (°C.) | IR spectrum (cm⁻¹) |
|---|---|---|---|---|---|
| 18 | −NH−C₆H₁₁ | −CH₂−C₆H₄(CH₃) (meta) | H | 144~145 | 3410, 1630 |
| 19 | −NH−C₆H₁₁ | −CH₂−C₆H₄−Cl (para) | H | oil | 3410, 3300, 1650 |
| 20 | −NH−C₆H₁₁ | −CH₂COOC₂H₅ | H | 113~116 | 3325, 1748, 1625 |
| 21 | −NH−C₆H₁₁ | −CH₂−C₆H₄−Cl (meta) | H | 144~148 | 3430, 1627 |
| 22 | −NH−C₆H₁₁ | −CH₂−C₆H₄−Cl (ortho) | H | 218~220 | 3430, 1635 |
| 23 | −NHCH₃ | −CH₂CH=CH₂ | −OCH₃ | 130~132 | 3360, 1605 |
| 24 | −NH−C₆H₅ | −CH₂CH=CH₂ | −OCH₃ | 146~149 | 3370, 1495 |
| 25 | 2,4-Cl₂−C₆H₃− | −CH₂CH=CH | −OCH₃ | 149~152 | 1605, 1580 |
| 26 | −OCH₃ | −CH₂CH=CH | −OCH₃ | 109~112 | 1645 |
| 27 | −NH−C₆H₅ | −CH₂CH=CH | −OCH₂CH₃ | 135~137 | 3400, 1640 |
| 28 | −O−C₆H₅ | −CH₂CH=CH₂ | −OCH₂CH₃ | 99~102 | 1659 |
| 29 | −NH−C₆H₅ | −CH₂CH=CH₂ | H | 136~138 | 3250, 1640 |

In using the compound of the present invention as a fungicide, it may be mixed with various carriers and formulated into various forms such as wettable powder, emulsion, dust, granules or suspension by a conventional method employed in the art.

The carrier may be selected from among liquid ones such as conventional organic solvents and solid ones such as conventional clay minerals and pumice. The formulation may further contain, for example, a surfactant to thereby give emulsifiability, dispersibility, spreadability or the like. Furthermore, it may be mixed with fertilizers or other agricultural chemicals such as insecticide, fungicide or the like.

In order to use the formulation as a fungicide, it is necessary to sufficiently apply the active compound in such a manner as to fully exert the desired effect. The amount of application thereof may range generally from 50 to 2000 g/ha, preferably from 200 to 1000 g/ha. The formulation may be in the form of a wettable powder, an emulsion, a dust, granules or a suspension containing 0.1 to 50% by weight of the active ingredient.

In preparing an emulsion, the active ingredient is dissolved in an agriculturally acceptable organic solvent and an emulsifier which is soluble in the solvent is then added thereto. Suitable examples of the solvent include xylene, o-chlorotoluene, cyclohexanone, isophorone, dimethylformamide, dimethylsulfoxide and mixtures thereof. Among these solvents, aromatic hydrocarbons and mixtures thereof with ketones and polar solvents are particularly suitable.

The surfactant to be used as an emulsifier may be used in an amount of from 1 to 20% by weight of the emulsion. Any of the anionic, cationic and nonionic surfactants may be selected therefor.

Examples of the anionic surfactants include salts of alkyl sulfates, alkyl diphenyl ether disulfonates, naphtylmethanesulfonates, lignin sulfonates, alkyl sulfosuccinates, alkylbenzenesulfonates and alkyl phosphates. Examples of the cationic surfactants include alkylamine salts and quaternary ammonium salts.

Examples of the nonionic surfactants include polyoxyethylene alkyl ethers, polyoxyethylene alkylaryl ethers, sorbitan fatty esters, polyoxyethylene sorbitan fatty esters, polyoxyethylene sorbitol fatty esters, glycerol fatty esters and polyoxyethylene fatty esters.

The concentration of the active ingredient may range from 0.5 to 20% by weight, preferably from 1 to 10% by weight.

A wettable powder may be formulated by adding the active ingredient to an inert solid carrier in the form of a fine powder and a surfactant. The content of the active ingredient may range from 2 to 50% by weight while the content of the surfactant may range from 1 to 20% by weight in general.

The solid carrier commonly mixed with the active ingredient may be selected from among natural clay, silicates, silica and alkaline earth metal carbonates. Typical examples thereof include kaolin, zieclite, talc, diatomaceous earth, magnesium carbonate, calcium carbonate, dolomite and the like.

Anionic surfactants, nonionic surfactants or mixtures thereof may be employed as an emulsifier, a spreader or a dispersant to be generally used for formulation of the wettable powder. Similar surfactants to those cited above regarding the emulsion may be used therefor.

A dust may be formulated by blending the active ingredient with inert carriers commonly used in the dust formulation, for example, talc, fine clay power, pyrophyllite, diatomaceous earth, magnesium carbonate or the like.

The concentration of the active ingredient may range from 0.1 to 20% by weight, preferably from 0.5 to 5% by weight.

Granules may be formulated by mixing the active ingredient with inert carriers in the form of a fine powder, such as bentonite, kaolin clay, diatomaceous earth or talc, kneading the mixture together with water and then granulating the same with a granulating machine. Alternatively, the granules may be prepared by dissolving the active ingredient together with a spreader, and depositing the resulting solution onto a granular carrier previously granulated to have the particle size of 15 to 30 mesh, or onto a granular mineral obtained by grinding natural pumice, acid clay or zeolite followed adjusting its particle size. These granules may contain 0.2 to 20% by weight, preferably 1 to 10% by weight, of the active ingredient.

A suspension may be prepared by finely powdering the active ingredient and mixing the same with a surfactant and water. As the surfactant to be used herein, any of the anionic, cationic and nonionic ones as well as mixtures thereof cited above regarding the preparation of the emulsion may be selected. It is generally used in an amount of from 1 to 20% by weight.

The active ingredient may be contained in an amount of from 1 to 50% by weight, preferably from 2 to 20% by weight.

EXAMPLES

To further illustrate the present invention, the following Examples will be given, in which "parts" represent part by weight.

| Formulation Example 1: Emulsion | |
| --- | --- |
| compound No. 24 | 10 parts |
| o-chlorotoluene | 50 parts |
| cyclohexanone | 36 parts |
| Sorpol* 900B | 4 parts |

(*trademark of surfactant manufactured by Toho Chemical Industry Co., Ltd.)

The above components were homogeneously mixed together and dissolved to thereby obtain an emulsion of the present invention.

| Formulation Example 2: Wettable powder | |
| --- | --- |
| compound No. 6 | 30 parts |
| kaolin clay | 63 parts |
| Sorpol 5039 | 5 parts |
| Sorpol 5060 | 2 parts |

The above components were mixed together and ground to thereby obtain a wettable powder of the present invention.

| Formulation Example 3: Dust | |
| --- | --- |
| compound No. 7 | 2 parts |
| kaolin clay | 98 parts |

The above components were mixed together and ground to thereby obtain a dust of the present invention.

| Formulation Example 4: Granules | |
| --- | --- |
| compound No. 1 | 5 parts |
| bentonite | 45 parts |

-continued

| Formulation Example 4: Granules | |
|---|---|
| talc | 45 parts |
| sodium ligninsulfonate | 5 parts |

The above components were homogeneously mixed together and ground. Then water was added thereto and the mixture was kneaded, granulated and dried to thereby obtain granules of the present invention.

| Formulation Example 5: Suspension | |
|---|---|
| compound No. 29 | 10 parts |
| ethylene glycol | 5 parts |
| Sorpol 3078 | 5 part |
| Sorpol 7512 | 0.5 part |
| water | 79.5 parts |

The above components were homogeneously mixed together and ground to thereby obtain a suspension of the present invention.

To illustrate the mycelium growth-inhibiting effect on typical molds and the plant disease-preventing effect of the compound of the present invention, the following Test Examples will be given.

Test Example 1: Mycelium growth-inhibiting effect on Petri dish

A solution of the compound of the present invention in dimethyl sulfoxide was added to a potato dextrose agar medium (PDA medium) to give a concentration of 100 ppm. Then a plate medium was prepared in a Petri dish of 9 cm in diameter. Two mycelia 4 mm in diameter, which had been cultured in a PDA medium, were placed on the agar medium and cultured at 25° C. for two days (in the case of *Pythium graminicola*), five days (in the case of *Fusarium oxysporum*) or three days (in the case of *Rhizoctonia solani*). Then the diameter of the obtained colony was compared with that of a control lot wherein no chemical was added and the growth inhibition ratio was calculated according to the following equation. Table 2 gives the results wherein each value is a mean value.

Growth inhibition ratio (%) =

$$\frac{\text{(Colony diameter of control lot)} - \text{(Colony diameter of test lot)}}{\text{(Colony diameter of control lot)}} \times 100$$

TABLE 2

| Compound No. | Species | | |
|---|---|---|---|
| | Pythium | Fusarium | Rhizoctonia |
| 1 | 100 | 53 | 51 |
| 2 | 100 | 80 | 75 |
| 3 | 98 | 60 | 50 |
| 4 | 100 | 60 | 76 |
| 5 | 100 | 68 | 70 |
| 6 | 100 | 57 | 69 |
| 7 | 100 | 56 | 56 |
| 8 | 100 | 80 | 70 |
| 9 | 100 | 80 | 56 |
| 10 | 90 | 32 | 56 |
| 11 | 100 | 62 | 74 |
| 12 | 15 | 4 | 11 |
| 13 | 60 | 50 | 70 |
| 14 | 15 | 10 | 20 |
| 15 | 59 | 9 | 19 |
| 16 | 68 | 27 | 49 |
| 17 | 55 | 9 | 26 |

TABLE 2-continued

| Compound No. | Species | | |
|---|---|---|---|
| | Pythium | Fusarium | Rhizoctonia |
| 18 | 59 | 6 | 25 |
| 19 | 63 | 8 | 31 |
| 20 | 75 | 41 | 45 |
| 21 | 53 | 3 | 43 |
| 22 | 57 | 7 | 32 |
| 23 | 100 | 53 | 51 |
| 24 | 80 | 40 | 50 |
| 25 | 11 | 5 | 24 |
| 26 | 59 | 35 | 61 |
| 27 | 13 | 23 | 13 |
| 28 | 12 | 15 | 4 |
| 29 | 56 | 33 | 31 |

Test Example 2: Preventive effect on cucumber downy mildew

A cucumber seedling (variety: Kashu No. 1) was grown in an unglazed pot of 9 cm in diameter. On reaching the trifoliate stage, 10 ml of a formulation of each compound prepared by the method of Formulation Example 1 (concentration: 100 ppm) was sprayed thereon with a spray gun. Three plants were employed per compound.

After drying for four hours, a spore suspension ($2 \times 10^5$/ml) of *Pseudoperonospora cubensis* causative of cucumber downy mildew was inoculated to the plants by spraying. Following the inoculation, each plant was cultured at 20° C. under moisture-saturated conditions for 12 hours and then at 20° C. at a relative humidity of 70 to 80% for six days. Seven days after the inoculation, lesions formed on the leaves of the monofoliate and difoliate stages were examined and the preventive value (%) was calculated according to the following equation. Table 3 gives the results.

$$\text{Preventive value (\%)} = \frac{\text{(Lesion rate of control lot)} - \text{(Lesion rate of test lot)}}{\text{(Lesion rate of control lot)}} \times 100$$

TABLE 3

| Compound No. | Preventive value (%) |
|---|---|
| 4 | 45 |
| 5 | 75 |
| 6 | 80 |
| 7 | 85 |
| 10 | 100 |
| 11 | 80 |
| 13 | 50 |
| 24 | 90 |
| 25 | 30 |
| 29 | 85 |

Test Example 3: Preventive effect on wheat powdery mildew:

A wheat seedling (variety: Norin No. 61) was grown in a pot of 9 cm in diameter. On reaching the difoliate stage, 20 ml of a formulation of each compound prepared by the method of Formulation Example 1 (concentration: 100 ppm) was sprayed thereon with a spray gun. 13 plants were employed per lot for each compound and two lots were employed for each compound.

One day after the spraying, each plant was inoculated with conidia of *Eryshiphe graminis* causative of wheat powder mildew by application. Following the inoculation, each plant was cultured at 20° C. under moisture-saturated conditions for 12 hours and then at 20° C. at 12 hour photoperiod for six days. Seven days after the inoculation, lesions formed on the leaves of the monofoliate and difoliate stages were examined and the preventive value (%) was calculated in the same manner as in the above-described Test Example 2. Table 4 gives the results.

TABLE 4

| Compound No. | Preventive value (%) |
| --- | --- |
| 1 | 85 |
| 2 | 75 |
| 4 | 95 |
| 6 | 95 |
| 7 | 85 |
| 8 | 50 |
| 12 | 50 |
| 13 | 75 |
| 14 | 50 |
| 28 | 75 |
| 29 | 75 |

As described above, the compound of the present invention exerts a growth-inhibiting effect of various molds, suppresses the occurrence of plant diseases and thus provides an effective means for elevating productivity without giving any chemical damage.

We claim:

1. A benzothiazole derivative of the formula:

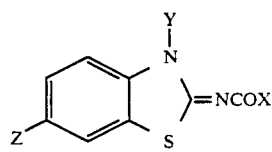

wherein X represents —NHR, —R or —OR in which R is $C_{1-4}$-alkyl, cyclohexyl, phenyl or dichlorophenyl; Y represents allyl, $C_{1-2}$-alkyloxycarbonylalkyl, benzyl, monochlorobenzyl or monomethylbenzyl; and Z represents $C_{1-2}$-alkoxy or a hydrogen atom.

2. An agricultural and horticultural fungicide in the form of an emulsion comprising a benzothiazole derivative as defined in claim 1 as an active ingredient, an organic solvent and an emulsifier.

3. An agricultural and horticultural fungicide in the form of a wettable powder comprising a benzothiazole derivative as defined in claim 1 as an active ingredient, an inert solid carrier in the form of a fine powder and a surfactant.

4. An agricultural and horticultural fungicide in the form of a dust or granule comprising a benzothiazole derivative as defined in claim 1 as an active ingredient and an inert carrier.

5. An agricultural and horticultural fungicide in the form of a a suspension comprising a benzothiazole derivative as defined in claim 1 as an active ingredient, a surfactant and water.

* * * * *